US00PP31138P2

(12) United States Plant Patent
Hansen

(10) Patent No.: US PP31,138 P2
(45) Date of Patent: Nov. 26, 2019

(54) ***AGAVE* PLANT NAMED 'ROYAL FLUSH'**

(50) Latin Name: ***Agave schidigera* (Zucc.)**
Varietal Denomination: Royal Flush

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,925

(22) Filed: Feb. 1, 2019

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden

(57) ABSTRACT

A new and unique *Agave* plant named 'Royal Flush' characterized by rigid narrow foliage that points upwardly and curves slightly inwardly toward apex. Leaves have slightly curly filifers in place of marginal teeth. Leaves are variegated with creamy yellow margins, sharply contrasting deep-green leaf centers and a faint minty green between the margin and center. The plant is useful in the landscape as a specimen, en masse, or also in a container in the home or landscape.

1 Drawing Sheet

Botanical classification: *Agave schidigera* (Zucc.).
Variety denomination: 'Royal Flush'.

STATEMENT REGARDING PRIOR DISCLOSURES UNDER 37 CFR 1.77(b)(6)

The first public disclosure of the claimed plant, in the form of a photograph and brief description on a website operated by Walters Gardens, Inc. on Feb. 1, 2018. The claimed plant was first sold on Jul. 23, 2018 by Walters Gardens, Inc., who obtained the plant and all information relating thereto, from the inventor. No plants of *Agave* 'Royal Flush' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct Variegated squid *Agave* plant, *Agave* 'Royal Flush' selected by Hans A. Hansen at a wholesale perennial nursery in Zeeland, Mich., USA as an uninduced whole-plant mutation from a tissue cultured crop of *Agave schidigera* 'Shira ito no Ohi' (not patented) (frequently referred to in the trade as 'Queen of White Thread') on Dec. 23, 2014. The new plant has been successfully asexually propagated by shoot tip tissue culture at a nursery in Zeeland, Mich. Shoot tip tissue culture propagation systems have been found produce stable and identical plants that maintain the unique characteristics of the original plant.

BRIEF SUMMARY OF THE INVENTION

*Agave* 'Royal Flush' differs from its parent, 'Shira ito no Ohi', as well as all other *Agaves* known to the applicant. 'Shira ito no Ohi' has a narrower creamy yellow to white margin and the center is darker green. The most similar *Agave* cultivars known to the inventor are: *Agave bracteosa* 'Stingray' U.S. Plant Pat. No. 30,280, and 'Shira ito no Ohi Nakafu' (not patented), *Agave multifilifera* 'Starshine' (not patented) and *Agave filifera* 'Cream Edge' (not patented). 'Stingray' has longer more arching and flexible foliage without filifers on the margin. 'Shira ito no Ohi Nakafu' is a smaller plant that has the lighter creamy yellow to white portion in the center of the leaves and green on the margins. 'Starshine' has narrower leaves and narrower variegated margins, the *filifera* are straighter. 'Cream Edge' has variegation that is not as wide, the leaf orientation is more outwardly.

*Agave* 'Royal Flush' differs from all other *Agaves* known to the applicant by the combined following traits:

1. Rigid linear foliage that is upright and curving inward toward leaf tips;
2. Leaves with small apical spines and without lateral spines;
3. Leaf margins have slightly curly filifers in place of marginal teeth;
4. Leaves have creamy yellow margins and contrasting deep green leaf centers.

BRIEF DESCRIPTION OF THE DRAWINGS

The photograph of the new plant demonstrates the overall appearance of the new plant including the unique traits as a three-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

The drawing shows the habit of the whole plant with foliage.

DETAILED BOTANICAL DESCRIPTION

The following descriptions and color references are based on the 2015 edition of The Royal Horticultural Society Colour Chart except where common dictionary terms are used. The new plant, *Agave* 'Royal Flush', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Mich. with supplemental water and fertilizer as needed.

Botanical classification: *Agave schidigera* (Zucc.);

Variety denomination: 'Royal Flush';

Sport parentage: *Agave schidigera* 'Shira ito no Ohi';

Propagation: Sterile plant tissue culture;

Time to initiate roots from tissue culture: About 28 days;

Growth rate: Slow;

Crop time: About 24 weeks to finish during the summer in a 3.8 liter container from an established 2.5 cm tissue culture plug;

Rooting habit: Fleshy, lightly branching, with roots up to 12 cm long;

Root color: Nearest RHS 158C;

Plant shape and habit: Herbaceous tender perennial with basal rosettes of narrow, acaulescent leaves emerging from central base, producing a symmetrical, rounded mound;

Plant size: Foliage height about 15.0 cm tall from soil line to the top of the leaves and about 14.5 cm wide at the widest point about 8.5 cm above soil line;

Foliage description: Linear, simple, fleshy; margins with filifers every 7.0 mm to 10.0 mm; narrowly acute apex ending in long firm spine; truncate sessile base; glabrous and slightly glaucous abaxial and adaxial; upright to slightly inwardly-curving;

Number of leaves: About 60 per plant;

Leaf size: To about 9.5 cm long, 18.0 cm wide near center; margin variegation to 6.0 mm wide at center of leaf, dark-green longitudinal middle of leaf to about 6.0 mm wide at center;

Leaf blade color:

*Mature adaxial*.—Margin nearest RHS 18C, center nearest RHS 139A; region between margin and center more green than RHS 191C or RHS 191D.

*Mature abaxial*.—Margin nearest RHS 146D and center nearest RHS 146C.

*Mature adaxial base*.—Margin nearest RHS 18B toward apex and between RHS 18C and RHS 18D toward base, center between RHS 136A and RHS 139A toward margin and in longitudinal middle nearest RHS 146B.

*Expanding young adaxial and abaxial coloration identical to mature.*

Filifers: Thin; stramineus; to about 25.0 mm long and 0.3 mm diameter; with small side branches less than 0.2 mm long and less than 0.1 mm thick;

Filifer color: Between RHS 159D and RHS 155D;

Foliage fragrance: None observed;

Stem: To about 1.7 cm wide and about 2.5 cm tall; covered with leaves;

Apical spine: Apical spine to about 5.0 mm long and 1.0 mm wide at base; firm;

Apical spine color: Nearest RHS 200A;

Marginal spines: Absent;

Petiole: Sessile;

Veins: Indistinguishable;

Flower description: Flowers have not yet been observed;

Fruit and seed: Have not yet been observed;

Disease resistance: *Agave* 'Royal Flush' has not been observed to be resistant to diseases common to *Agaves* beyond that which is normal for *Agave*. The plant is xeromorphic and survives well with minimal water once established. Hardiness at least from USDA zone 8 to 10. Extent of winter hardiness has not been tested.

I claim:

1. A new and distinct cultivar of ornamental *Agave* plant named 'Royal Flush' as herein described and illustrated.

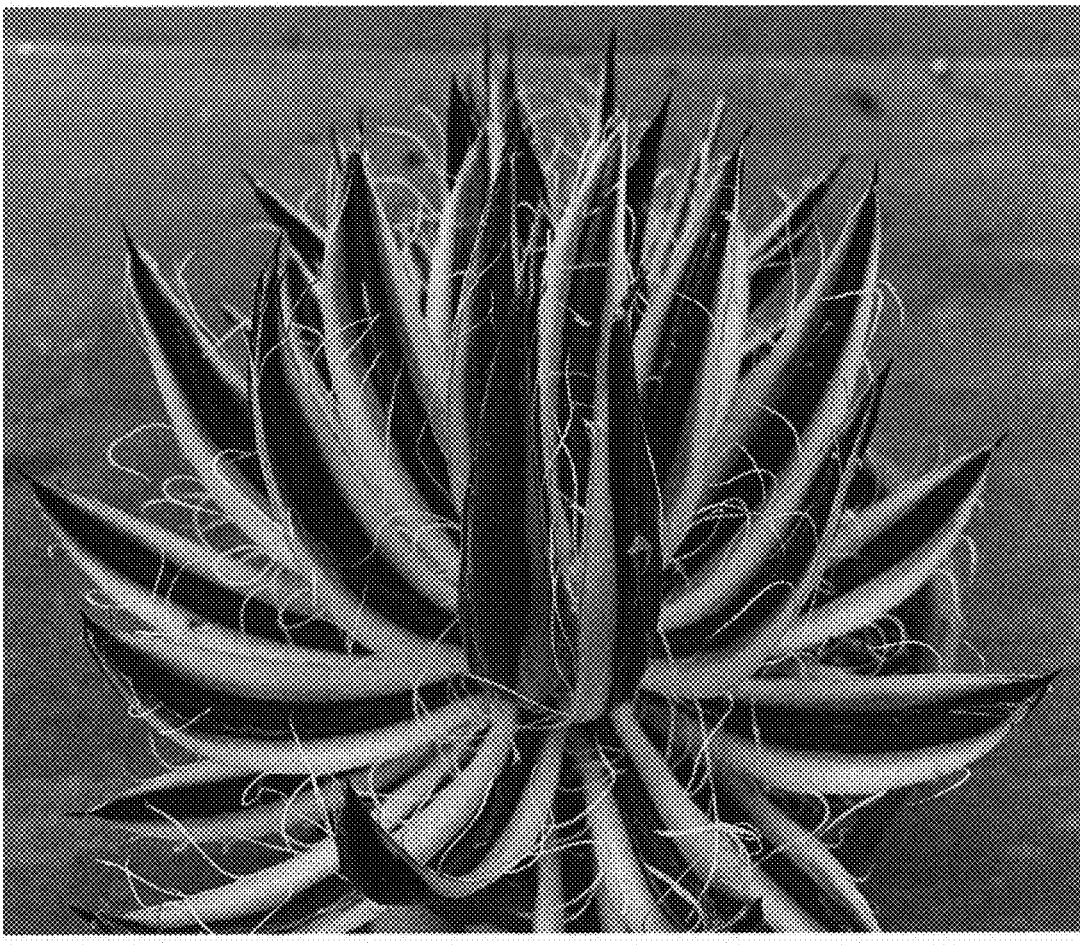

* * * * *